US012544582B2

(12) United States Patent
Lee

(10) Patent No.: US 12,544,582 B2
(45) Date of Patent: Feb. 10, 2026

(54) RF ELECTRODE CARTRIDGE FOR SKIN BEAUTY CARE TREATMENT AND HANDPIECE FOR SKIN BEAUTY CARE TREATMENT PROVIDED WITH SAME

(71) Applicant: CLASSYS INC., Seoul (KR)

(72) Inventor: Seok Joo Lee, Seoul (KR)

(73) Assignee: CLASSYS INC., Seoul (KR)

( * ) Notice: Subject to any disclaimer, the term of this patent is extended or adjusted under 35 U.S.C. 154(b) by 788 days.

(21) Appl. No.: 17/798,723

(22) PCT Filed: Feb. 11, 2020

(86) PCT No.: PCT/KR2020/001880
§ 371 (c)(1),
(2) Date: Aug. 10, 2022

(87) PCT Pub. No.: WO2021/162136
PCT Pub. Date: Aug. 19, 2021

(65) Prior Publication Data

US 2023/0084740 A1 Mar. 16, 2023

(51) Int. Cl.
*A61N 1/40* (2006.01)
*A61H 23/02* (2006.01)

(52) U.S. Cl.
CPC ........... *A61N 1/40* (2013.01); *A61H 23/0254* (2013.01); *A61H 2201/0153* (2013.01); *A61H 2201/0214* (2013.01); *A61H 2201/0242* (2013.01); *A61H 2201/10* (2013.01); *A61H 2201/5082* (2013.01)

(58) Field of Classification Search
CPC .................. A61N 1/40; A61H 23/0254; A61H 2201/0153; A61H 2201/0214; A61H 2201/0242; A61H 2201/10; A61H 2201/5082
See application file for complete search history.

(56) References Cited

U.S. PATENT DOCUMENTS

| | | | |
|---|---|---|---|
| 8,636,725 B2 | 1/2014 | Amann et al. |
| 2017/0007254 A1 | 1/2017 | Jaworek et al. |

FOREIGN PATENT DOCUMENTS

| | | | |
|---|---|---|---|
| AU | 2004226484 A2 | 10/2004 |
| BR | PI0403032 A | 6/2005 |
| BR | 112018011204 B1 | 10/2022 |
| CN | 1627923 A | 6/2005 |
| JP | 2006-204767 A | 8/2006 |
| JP | 2015-157092 A | 9/2015 |
| KR | 10-2005-0114676 A | 12/2005 |
| KR | 10-2013-0077135 A | 7/2013 |
| KR | 10-2017-0064458 A | 6/2017 |
| KR | 10-1757593 B1 | 7/2017 |
| WO | 2009/100366 A2 | 8/2009 |

*Primary Examiner* — Linda C Dvorak
*Assistant Examiner* — Abigail Bock
(74) *Attorney, Agent, or Firm* — WHDA, LLP

(57) ABSTRACT

Proposed is an RF electrode cartridge for skin beauty care treatment and a handpiece for skin beauty care treatment provided with the same. While being freely tilted for all ranges of 360 angle degrees around a ball joint part 140 within a radius thereof, the RF electrode body 120 moves in a state of being brought into close contact with the skin during the procedure, thereby preventing an accident that may occur while the RF electrode body 120 is spaced apart from the skin and in which damage to the skin tissue or burns to the skin may be caused. Accordingly, the present disclosure may greatly improve safety during a procedure.

7 Claims, 6 Drawing Sheets

RF ELECTRODE CARTRIDGE FOR SKIN BEAUTY CARE TREATMENT AND HANDPIECE FOR SKIN BEAUTY CARE TREATMENT PROVIDED WITH SAME

TECHNICAL FIELD

The present disclosure relates to an RF electrode cartridge for skin beauty care treatment and a handpiece for skin beauty care treatment provided with the same. In particular, the present disclosure relates to an RF electrode cartridge for skin beauty care treatment and a handpiece for skin beauty care treatment provided with the same that may prevent burns during a procedure by bringing an RF electrode in close contact with skin during the procedure.

BACKGROUND ART

In general, a handpiece provided with an RF electrode is a device configured to heat skin and underlying tissues of the skin using an RF (radio frequency) electrode, thereby treating same.

The handpiece provided with an RF electrode is used for skin care treatment to restore the skin by increasing temperature of the skin after a cryolipolysis procedure as an obesity treatment and to heat the skin and the underlying tissues of the skin to cause contraction of collagen or induce a wound healing reaction of the collagen.

In recent years, due to increasing interest in skin beauty treatment, the handpiece provided with the RF electrode is used in a variety of ways for skin remodeling/resurfacing and wrinkle removal, and for the treatment and the like of sebaceous glands, hair follicle adipose tissue, and spider veins, by the contraction or the wound healing response of the collagen in the lower dermis.

On the other hand, the handpiece provided with the RF electrode in a procedure using the RF electrode needs to perform the procedure in a state in which the RF electrode is brought into close contact with the patient's skin.

When a portion of the RF electrode comes off the patient's skin during the procedure, a rapid temperature rise in the skin tissue is induced so that there is a risk that the patient's skin tissue may be damaged by heat or the skin may be burned.

Accordingly, the surgeon who is the operator has to frequently check whether the RF electrode of the handpiece provided with the RF electrode is brought into close contact with the skin during the procedure, so there is a problem in that the treatment takes a long time, and the psychological fatigue of the operator during the treatment is significant.

In addition, since the operator performs the procedure by pressing the handpiece provided with the RF electrode by applying a lot of force to bring an entire surface of the RF electrode into close contact with the skin, there were problems in that the patient may feel uncomfortable, and at the same time, joint diseases may be caused to the operator's wrist and the like so that the operator may not perform stable long-term treatment.

DISCLOSURE

Technical Problem

Accordingly, the present disclosure has been made keeping in mind the above problems occurring in the related art, and an objective of the present disclosure is to provide an RF electrode cartridge for skin beauty care treatment and a handpiece for skin beauty care treatment provided with the same, in which an RF electrode body is freely tilted for all ranges of 360 angle degrees within a radius thereof by a ball joint and is moved in a state of being brought into close contact with skin during a procedure.

Another objective of the present disclosure is to provide the RF electrode cartridge for skin beauty care treatment and the handpiece for skin beauty care treatment provided with the same, with which the operator may operate the procedure while freely moving the RF electrode body that is in a state of being brought into close contact with the skin by an appropriate force during the procedure, whereby the operator's convenience is secured, and at the same time, the patient's discomfort due to excessive pressure is prevented.

Technical Solution

In order to achieve the above objectives, one embodiment of an RF electrode cartridge for skin beauty care treatment according to the present disclosure may include: a cartridge casing; and an RF electrode body positioned on one surface of the cartridge casing and being brought into contact with skin to apply RF energy inside the skin, wherein the cartridge casing includes: a first casing part on one surface of which the RF electrode body is positioned; and a second casing part to which the first casing part is connected to be tiltable.

The one embodiment of an RF electrode cartridge for skin beauty care treatment according to the present disclosure may further include a ball joint part connecting the first casing part and the second casing part, thereby allowing the first casing part to be freely tilted for all ranges of 360 angle degrees within a radius of the first casing part.

The one embodiment of an RF electrode cartridge for skin beauty care treatment according to the present disclosure may further include a bellows member having one end part side connected to the first casing part and an opposite end part side connected to the second casing part, positioned to surround the ball joint part, and provided with a plurality of corrugation parts.

The one embodiment of an RF electrode cartridge for skin beauty care treatment according to the present disclosure may further include a vibration motor unit positioned inside the cartridge casing.

In the present disclosure, the RF electrode body may include an RF electrode member positioned on one surface of the first casing part and provided in a curved convex surface as a conductor to apply RF energy to the skin; and an insulation film member covering a surface of the RF electrode member.

In the present disclosure, the RF electrode member may be a plating layer integrally provided in plating on one surface of the first casing part.

In the present disclosure, a cooling space filled with coolant for cooling the RF electrode body may be positioned inside the first casing part, a first coolant line part and a second coolant line part supplying the coolant into the cooling space and discharging the coolant inside the cooling space so as to circulate the coolant may be further included, and a temperature sensor configured to sense temperature of the coolant may be positioned inside the cooling space.

In the present disclosure, a cooling space filled with coolant for cooling the RF electrode body may be positioned inside the first casing part, the RF electrode body may be provided with a first connection terminal that protrudes upward and may be electrically connected to an RF signal generator of a control main body, and a terminal passage through which the first connection terminal passes may be provided in the cooling space, and a terminal insulation part may be positioned to insulate the first connection terminal from the coolant in the cooling space.

In the present disclosure, in the cooling space protruding integrally from a bottom surface of the cooling space and having an upper end part side thereof connected to a cooling space cover part that seals an upper part of the cooling space, thereby being sealed, the terminal insulation part may have a structure insulating the coolant and the first connection terminal.

In order to achieve the above objectives, one embodiment of a handpiece for skin beauty care treatment according to the present disclosure may include: an RF electrode cartridge including an RF electrode body being brought into contact with skin; and a handpiece main body casing with which the RF electrode cartridge may be coupled to be detachable and which may be connected to a control main body, wherein, the RF electrode cartridge may include: a cartridge casing; and an RF electrode body positioned on one surface of the cartridge casing and being brought into contact with skin to apply RF energy inside the skin, wherein the cartridge casing may include: a first casing part on one surface of which the RF electrode body may be positioned; and a second casing part to which the first casing part may be connected to be tiltable.

The one embodiment of a handpiece for skin beauty care treatment according to the present disclosure may further include a ball joint part connecting the first casing part and the second casing part, thereby allowing the first casing part to be freely tilted for all ranges of 360 angle degrees within a radius of the first casing part.

The one embodiment of a handpiece for skin beauty care treatment according to the present disclosure may further include a bellows member having one end part side connected to the first casing part and an opposite end part side connected to the second casing part, positioned to surround the ball joint part, and provided with a plurality of corrugation parts.

The one embodiment of a handpiece for skin beauty care treatment according to the present disclosure may further include a vibration motor unit positioned inside the cartridge casing.

In the present disclosure, the RF electrode body may include: an RF electrode member positioned on one surface of the first casing part and provided in a curved convex surface as a conductor to apply RF energy to the skin; and an insulation film member covering the surface of the RF electrode member.

In the present disclosure, a cooling space filled with coolant for cooling the RF electrode body may be positioned inside the first casing part, a temperature sensor configured to sense temperature of the coolant may be positioned inside the cooling space. The temperature sensor may detect the temperature of the coolant and transmit the temperature to a controller in the control main body, and the controller may control an operation of a pump configured to circulate the coolant and the cooler configured to cool the coolant in circulation.

In the present disclosure, a cooling space filled with coolant for cooling the RF electrode body may be positioned inside the first casing part, the RF electrode body may be provided with a first connection terminal that may protrude upward and may be electrically connected to an RF signal generator of the control main body, and a terminal passage through which the first connection terminal passes may be provided in the cooling space, and a terminal insulation part may be positioned to insulate the first connection terminal from the coolant in the cooling space.

In the present disclosure, in the cooling space protruding integrally from a bottom surface of the cooling space and having an upper end part side thereof connected to a cooling space cover part that seals an upper part of the cooling space, thereby being sealed, the terminal insulation part may have a structure insulating the coolant and the first connection terminal.

In the present disclosure, a cartridge insertion part which the RF electrode cartridge is inserted into and coupled with may be positioned at a fore tip part of the handpiece main body casing, a cartridge coupling block, with which the RF electrode cartridge is coupled and which electrically connects the control main body and the RF electrode body, may be positioned to be movable inside the cartridge insertion part, and the cartridge coupling block may be positioned in a state elastically supported by a spring member for a cartridge.

In the present disclosure, a cartridge movement guide part configured to guide a linear movement of the cartridge coupling block may be positioned inside the handpiece main body casing.

In the present disclosure, the cartridge movement guide part may include: a movement guide bar part positioned to protrude from the cartridge coupling block; and a movement guide block positioned in the handpiece main body casing and with which the movement guide bar part is coupled to be movable by passing therethrough, wherein a plurality of the movement guide bar parts may be provided, and at least any one of the plurality of the movement guide bar parts may be positioned passing through the spring member for a cartridge.

Advantageous Effects

As described above, in the present disclosure, while being freely tilted for all ranges of 360 angle degrees around a ball joint part within a radius thereof, the RF electrode body moves in a state of being brought into close contact with the skin during the procedure, thereby preventing an accident that may occur while the RF electrode body is spaced apart from the skin and in which damage to the skin tissue or burns to the skin may be caused. Accordingly, the present disclosure has an effect of greatly improving safety during a procedure.

The present disclosure has an effect such that the operator may operate the procedure while freely moving the RF electrode body that is in a state of being brought into close contact with the skin by an appropriate force during the procedure, whereby the operator's convenience is secured, and at the same time, the patient's discomfort due to excessive pressure is prevented to greatly improve patient's satisfaction with a procedure.

Figure 1:
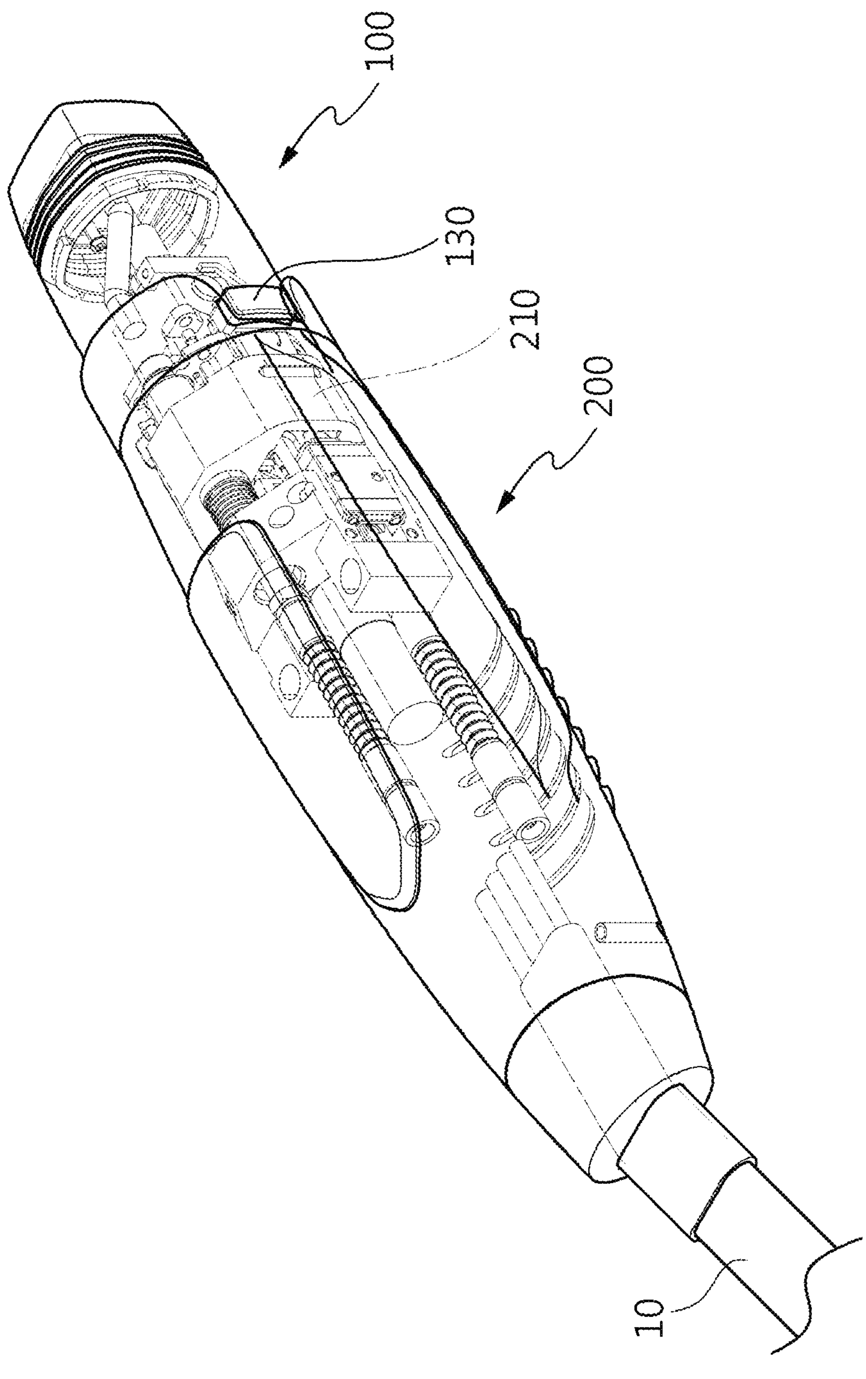
FIG. 1 is a perspective view showing an embodiment of a handpiece for skin beauty care treatment provided with an RF electrode cartridge for skin beauty care treatment according to the present disclosure.

<Description of the Main Reference Numerals in the Drawings>

| | |
|---|---|
| 100: RF electrode cartridge | 110: Cartridge casing |
| 110a: First casing part | 110b: Second casing part |
| 111: Cooling space | 112: Temperature sensor |
| 113: Terminal insulation part | 114: Cooling space cover part |
| 114a: Ball coupling part | 120: RF electrode body |
| 121: RF electrode member | 121a: First connection terminal |
| 122: Insulation film member | 130: Cartridge lock part |
| 140: Ball joint part | 150: Bellows member |
| 160: Vibration motor unit | 170: First coolant line part |
| 180: Second coolant line part | 200: Handpiece main body casing |
| 200a: Coolant circulation lines | 200b: Cartridge insertion part |
| 210: Cartridge coupling block | 211: Second connection terminal part |
| 212: Line connection part | 220: Spring member for a cartridge |
| 230: Cartridge movement guide part | 231: Movement guide bar part |
| 232: Movement guide block | |

BEST MODE

The present disclosure will be described in more detail.

An exemplary embodiment of the present disclosure will be described below in detail with reference to the accompanying drawings. Prior to a detailed description of the present disclosure, terms or words used in the present specification and claims, which are described below, should not be construed as being limited to conventional or dictionary meanings. Accordingly, configuration shown in the embodiments and drawings described in the present specification is only the most exemplary embodiment of the present disclosure and does not represent all the technical spirit of the present disclosure, so it should be understood that there may be various equivalents and variations that may be substituted for the configuration at the time of the present application.

Figure 2:
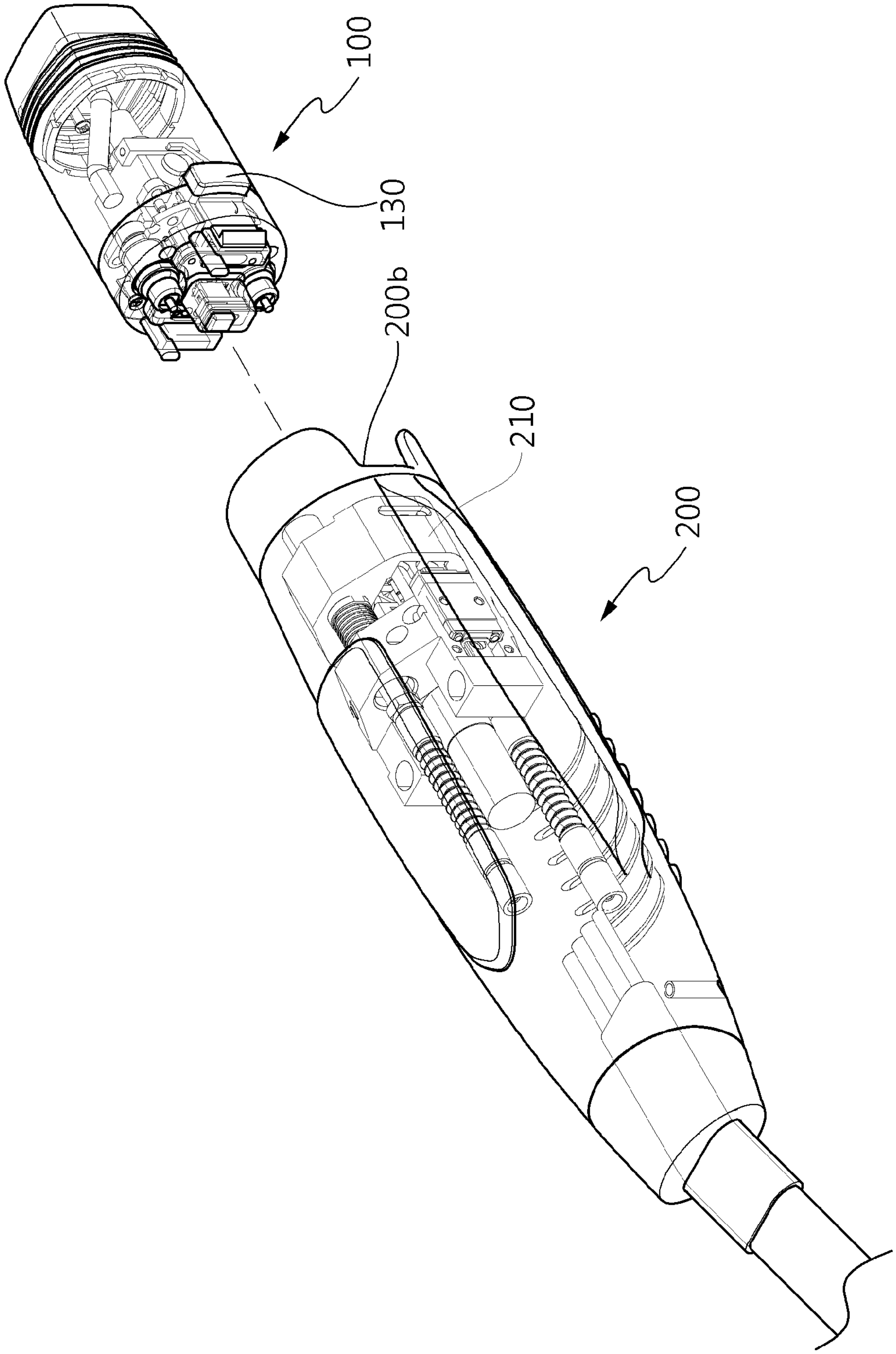
FIG. 2 is an exploded perspective view showing the embodiment of a handpiece for skin beauty care treatment provided with an RF electrode cartridge for skin beauty care treatment according to the present disclosure.

FIG. 1 is a perspective view showing an embodiment of a handpiece for skin beauty care treatment provided with an RF electrode cartridge for skin beauty care treatment according to the present disclosure, and FIG. 2 is an exploded perspective view showing the embodiment of a handpiece for skin beauty care treatment provided with an RF electrode cartridge for skin beauty care treatment according to the present disclosure and is a view showing an example in which a handpiece main body part and the RF electrode cartridge 100 for skin beauty care treatment are separated.

With reference to FIGS. 1 and 2, one embodiment of the handpiece for skin beauty care treatment provided with the RF electrode cartridge 100 for skin beauty care treatment according to the present disclosure includes: the RF electrode cartridge 100 including an RF electrode body 120 being brought into contact with skin; and a handpiece main body casing 200 with which the RF electrode cartridge 100 is coupled to be detachable and which is connected to a control main body.

The handpiece main body casing 200 is connected to the control main body with a connection cable, and the control main body is a known configuration that includes an RF signal generator applying electric power to the RF electrode body 120 and applying AC power to the RF electrode body to generate an RF signal, thereby being able to be implemented with various modifications thereof. Accordingly, it should be noted that a more detailed description will be omitted for the control main body.

In the handpiece for skin beauty care treatment provided with the RF electrode cartridge 100 for skin beauty care treatment according to the present disclosure, in a state of holding the handpiece with a hand and putting the RF electrode body 120 to be brought into contact with the skin, the operator may cause in the control main body an RF signal generator to apply AC power to the electrode body 120 to generate an RF signal so that the dermis inside the skin is heated to treat the skin or induce a beauty care treatment effect.

At this time, on the opposite side of the handpiece for skin beauty care treatment provided with the RF electrode cartridge 100 for skin beauty care treatment according to the present disclosure, an RF electrode panel body (not shown) having a larger area than the RF electrode body 120 may be positioned.

The RF electrode panel body is a known configuration that may heat the dermis inside the skin by applying an RF signal to treat the skin or cause a beauty care treatment effect. Accordingly, it should be noted that a more detailed description of the RF electrode panel body will be omitted.

That is, in a state in which the RF electrode body 120 is brought into contact with the skin, the handpiece for skin beauty care treatment according to the present disclosure applies an RF signal to the skin to heat the tissue inside the skin, so that skin remodeling/resurfacing, wrinkle removal, and treatment of sebaceous glands, hair follicle adipose tissue, and spider veins may be performed with a contraction or wound healing response of the collagen in the lower dermis.

The RF electrode cartridge 100, which is unable to be used for skin care treatment due to the end of its lifespan when used for a preset period of time for the treatment and thus is to be replaced, is a consumable and is coupled to be detachable with the handpiece main body casing 200.

A cartridge insertion part 200*b* which a portion of the RF electrode cartridge 100 is inserted into and coupled with is positioned at a fore tip part of the handpiece main body casing 200.

The RF electrode cartridge 100 is inserted into the cartridge insertion part 200*b* and is coupled to the cartridge coupling block 210 positioned in the cartridge insertion part 200*b*, thereby being locked by the cartridge lock part 130 at the final coupling position so that coupling is finished.

A pair of cartridge lock parts 130 uses a known configuration in which a wedge part that is configured to hook and support the cartridge coupling block 210 is positioned at a button part elastically supported by a pair of button-type lock parts positioned on opposite sides of a cartridge casing 110, and the lock is released when the button part is pressed. Accordingly, it should be noted that a more detailed description of the cartridge lock parts is omitted.

Figure 3:
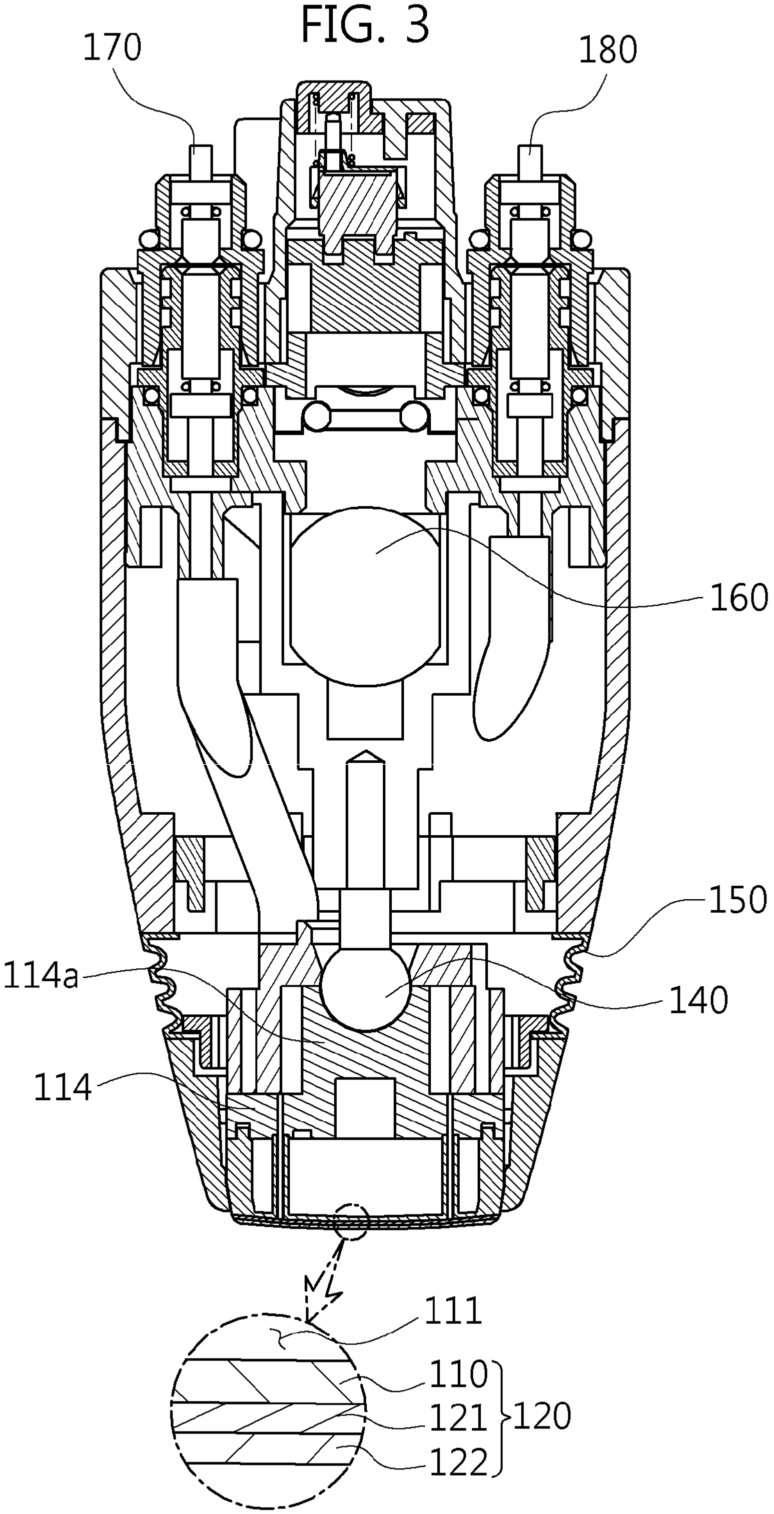
FIG. 3 is a sectional view showing an embodiment of the RF electrode cartridge for skin beauty care treatment according to the present disclosure.

FIG. 3 is a sectional view showing an embodiment of the RF electrode cartridge 100 for skin beauty care treatment according to the present disclosure. With reference to FIG.

3, one embodiment of the RF electrode cartridge 100 for skin beauty care treatment according to the present disclosure includes the cartridge casing 110 coupled to be detachable with the handpiece main body casing 200 and the RF electrode body 120 positioned on one surface of the cartridge casing 110 and being brought into contact with the skin to apply RF energy to the inside of the skin.

The RF electrode body 120 is positioned on an electrode mounting surface positioned on one end part side of the cartridge casing 110.

It is noted that the electrode mounting surface of the cartridge casing 110 is a surface facing the skin of the patient to be treated, that is, a surface positioned at the end part side facing the skin when the operator holds the handpiece main body casing 200 and performs the procedure.

The RF electrode body 120 may include an RF electrode member 121 that is positioned on the electrode mounting surface and is made of a conductor, thereby applying RF energy to the inside of the skin, and an insulation film member 122 that covers the surface of the RF electrode member 121.

The RF electrode member 121 is integrally attached to the electrode mounting surface together with a plating layer and the like so as to have a structure, which is integral with the cartridge casing 110 and has rigidity not to be deformed. Accordingly, the thickness of the RF electrode member 121 may be minimized.

In addition, as an example, the RF electrode member 121 is a plating layer integrally provided in plating on the electrode mounting surface of the cartridge casing 110.

The RF electrode body 120 has a curved surface to be convex toward the lower side and is provided also to have a curved surface that is not deformed even when pressed by the skin.

As an example, the surface curvature of the RF electrode body 120 is provided to have a curvature that may maximize an area of the RF electrode body 120 being brought into contact with the skin when pressed against the skin.

In addition, the RF electrode body 120 is provided in a shape having a curved surface with the surface to be convex, that is, a shape having an even curvature from a center to a circumference for all ranges of 360 angle degrees, so that the pressing force may be evenly distributed when the skin is pressed, and at the same time, the skin at the outer circumferential edge may be prevented from having pain with the skin being excessively pressed.

The RF electrode body 120 is provided to establish a curved surface that is not deformed when pressed against the skin, thereby maximizing an area being brought into close contact with the skin when the skin is pressed and, at the same time, being allowed not to be deformed during use so as to ensure durability.

The electrode mounting surface of the cartridge casing 110 has a curved surface to be convex toward the lower part side and is provided to establish a curved surface that is not deformed when pressed against the skin, thereby allowing the RF electrode member 121 provided by plating on the surface thereof to be provided in a curved surface to be convex toward the lower part side.

On the other hand, the cartridge casing 110 includes a first casing part 110*a* on which the RF electrode body 120 is positioned on one surface and a second casing part 110*b* to which the first casing part 110*a* is connected to be tiltable, whereby the RF electrode body 120 may be allowed to be maintained in a state of being brought into contact with the skin while being tilted when moved by being brought into contact with the skin.

The second casing part 110*b* is a part coupled to be detachable with the handpiece main body casing 200. Here, the second casing part 110*b* has a casing coupling part positioned on one end part side thereof, wherein the casing coupling part is inserted into the cartridge insertion part 200*b* of the handpiece main body casing 200 and coupled with the cartridge coupling block 210.

In addition, the first casing part 110*a* is connected to an opposite end part side of the second casing part 110*b* to be tiltable.

In more detail, the RF electrode cartridge 100 for skin beauty care treatment according to the present disclosure further includes a ball joint part 140 that connects the first casing part 110*a* and the second casing part 110*b* so that the first casing part 110*a* may be freely tilted for all ranges of 360 angle degrees of the first casing part.

As an example, the ball joint 140 is fixed to the opposite end part side of the second casing part 110*b* and has a ball body coupled to the first casing part 110*a* to be rotatable positioned at one end part side thereof.

A ball insertion part into which the ball body is inserted is positioned to be rotatable in the first casing part 110*a*, and the first casing part 110*a* may be freely tilted for all ranges of 360 angle degrees around the ball body within a radius thereof.

In addition, an embodiment of the RF electrode cartridge 100 for skin beauty care treatment according to the present disclosure may further include a bellows member 150 having one end part side connected to the first casing part 110*a* and an opposite end part side connected to the second casing part 110*b*, positioned to surround the ball joint part 140, and provided with a plurality of corrugation parts.

The bellows member 150 has the plurality of corrugation parts positioned in the longitudinal direction of the handpiece for skin beauty care treatment and supports the tilting operation of the first casing part 110*a* while the corrugation parts are freely folded and unfolded.

The bellows member 150 has one end part side fixed along the outer periphery of the first casing part 110*a* and an opposite end part side fixed along an outer circumference of the second casing part 110*b*, thereby surrounding the outer side of the ball joint part 140 positioned in the center at a spaced apart position.

The bellows member 150 surrounds the outside of the ball joint part 140 at the spaced position, whereby the first casing part 110*a* may be freely tilted for all ranges of 360 angle degrees around the ball body within a radius thereof, and covers between the first casing part 110*a* and the second casing part 110*b* to block foreign substances entering inside the first casing part 110*a* and the second casing part 110*b*.

In addition, the RF electrode cartridge 100 for skin beauty care treatment according to the present disclosure may further include a vibration motor unit 160 positioned inside the cartridge casing 110, and the vibration motor unit 160 may generate vibrations during the procedure to further improve the therapeutic effect with a massage effect on the skin with which the RF electrode body 120 is brought in close contact.

Figure 4:
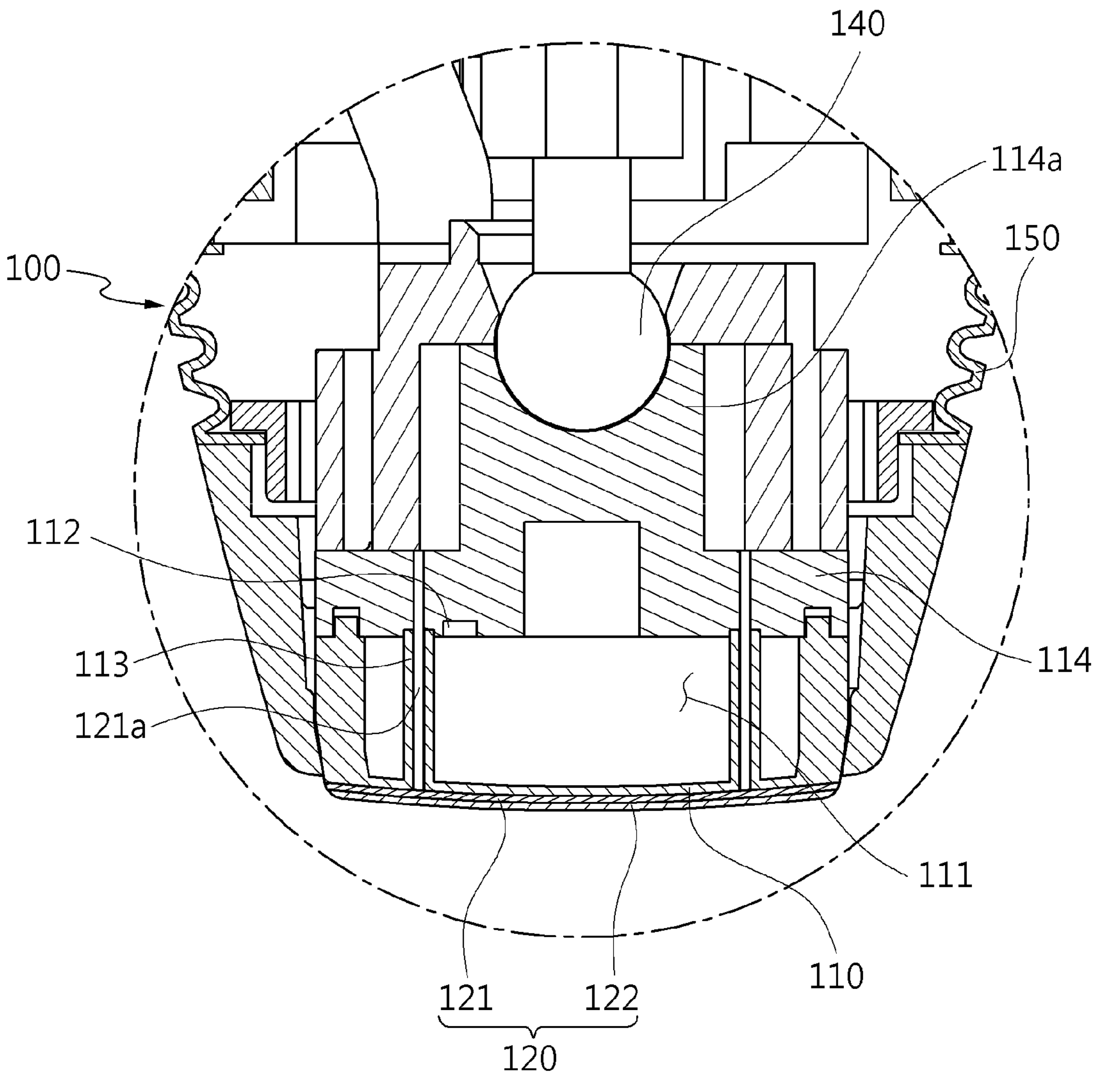
FIG. 4 is an enlarged sectional view showing the embodiment of the RF electrode cartridge for skin beauty care treatment according to the present disclosure.

On the other hand, FIG. 4 is an enlarged sectional view showing the embodiment of the RF electrode cartridge 100 for skin beauty care treatment according to the present disclosure. With reference to FIGS. 3 and 4, a cooling space 111 filled with coolant therein for cooling the RF electrode body 120 is positioned inside the cartridge casing 110, and the RF electrode cartridge 100 for skin beauty care treatment according to the present disclosure includes a first coolant line part 170 and a second coolant line part 180 configured to supply coolant to the inside of the cooling space 111 and to discharge the coolant in the cooling space 111, thereby circulating the coolant.

The cooling space 111 is positioned such that the electrode mounting surface is included in the first casing part 110*a* in which the RF electrode body 120 is positioned.

The first coolant line part 170 and the second coolant line part 180 are respectively connected to the coolant circulation lines positioned in the handpiece for skin beauty care treatment when the RF electrode cartridge 100 for skin beauty care treatment according to the present disclosure is coupled with the handpiece for skin beauty care treatment.

The first coolant line part 170 and the second coolant line part 180 are each positioned to protrude toward an upper part side of the cartridge casing 110 and has a structure configured to be connected to the corresponding coolant circulation line when the casing coupling part is inserted inside the cartridge insertion part 200*b* and coupled to the cartridge coupling block 210.

The coolant circulation line parts 200*a* are connected to a coolant tank positioned in the control main body. The first coolant line part 170 and the second coolant line part 180 are connected to the coolant tank positioned inside the control main body through the coolant circulation line parts 200*a.*

The coolant is circulated passing through the coolant tank and the cooling space 111 through an operation of a pump through the coolant circulation line parts 200*a*, the first coolant line part 170, and the second coolant line part 180. At this time, the coolant may be cooled during circulation by a cooler positioned in the coolant circulation lines or coolant tank, thereby being maintained to a constant temperature within the cooling space 111.

The cooler may include a known cooling device such as a radiator, a chiller, or the like for cooling the coolant.

In addition, a temperature sensor 112 configured to sense the temperature of the coolant is positioned inside the cooling space 111, and the temperature sensor detects the coolant temperature thereby transmitting the coolant temperature to a controller in the control main body.

The controller may control the operation of the pump and the cooler through the temperature information of the coolant received from the temperature sensor, thereby maintaining the temperature of the coolant inside the cooling space 111 to a temperature suitable for cooling the skin during the treatment.

As an example, the temperature sensor 112 is positioned inside the cooling space 111 to measure the temperature of the coolant at which the skin is substantially cooled and to maintain the temperature of the coolant at a temperature suitable for cooling the skin. In addition, it should be noted that the temperature sensor 112 may also be positioned anywhere capable of measuring the temperature of the coolant such as the coolant circulation lines, the coolant tank, or the like so as to measure the temperature.

While being discharged from the inside of the cooling space 111 by the operation of the pump, then cooled by the cooler after passing through the coolant tank, and then flowed again into the inside of the cooling space 111, the coolant may cool the skin surface when the skin is heated due to the application of an RF signal.

That is, the surface of the skin being treated is cooled by lowering the temperature of the RF electrode member 121 heated during the procedure with the circulating coolant, whereby it is possible to prevent burns and heat damage to the skin during the treatment.

The RF electrode cartridge 100 for skin beauty care treatment according to the present disclosure is able to circulate the coolant inside the cooling space 111 to continuously and stably cool the skin with the circulating coolant and to cool the skin to an even and constant temperature, so it is possible during the skin treatment to minimize discomfort caused by skin cooling and improve treatment satisfaction.

On the other hand, the RF electrode member 121 may be provided with a first connection terminal 121*a* that protrudes upward and is electrically connected to the RF signal generator of the control main body.

A plurality of the first connection terminals 121*a* is respectively positioned, and a lower end of each of the first connection terminals 121*a* passes through the cartridge casing 110 and is connected to the RF electrode body 120.

In addition, the first connection terminal 121*a* may pass through the cooling space 111 to protrude to the upper portion of the cartridge casing, thereby being electrically connected to the control main body.

In the cooling space 111, a terminal passage through which the first connection terminal 121*a* passes is provided, and a terminal insulation part 113 that insulates the first connection terminal 121*a* from the coolant inside the cooling space 111 is positioned.

A cooling space cover part, in which the ball coupling part 114*a* configured to be coupled to the ball joint part is positioned to protrude upward, is positioned on an upper part side of the cooling space 111. Accordingly, the cooling space 111 has a structure having the inside sealed.

In the structure protruding integrally from a bottom surface of the cooling space 111 and having an upper end part side thereof connected to a cooling space cover part that seals an upper part of the cooling space 111, whereby the cooling space is sealed, the terminal insulation part 113 is able to position the first connection terminal 121*a* to be able to be electrically connected to the control main body from the outer side of the cooling space 111 in a state of being insulated from the coolant by passing through the cooling space 111.

In the present disclosure, the RF electrode body 120 is integrally provided as a plating layer on the lower surface of the electrode support body, so that the manufacturing process may be simplified and the manufacturing cost may be reduced, thereby securing economic feasibility.

In addition, in the present disclosure, the RF electrode body 120 has a fixed shape that is not deformed by being pressed even when pressed by the skin, thereby securing the durability thereof.

In addition, in the present disclosure, the coolant is circulated, whereby a constant skin surface temperature may be maintained by cooling the skin surface heated with the RF signal, thereby minimizing the discomfort caused by skin cooling during the treatment and improving treatment efficiency and satisfaction during the treatment.

Figure 5:
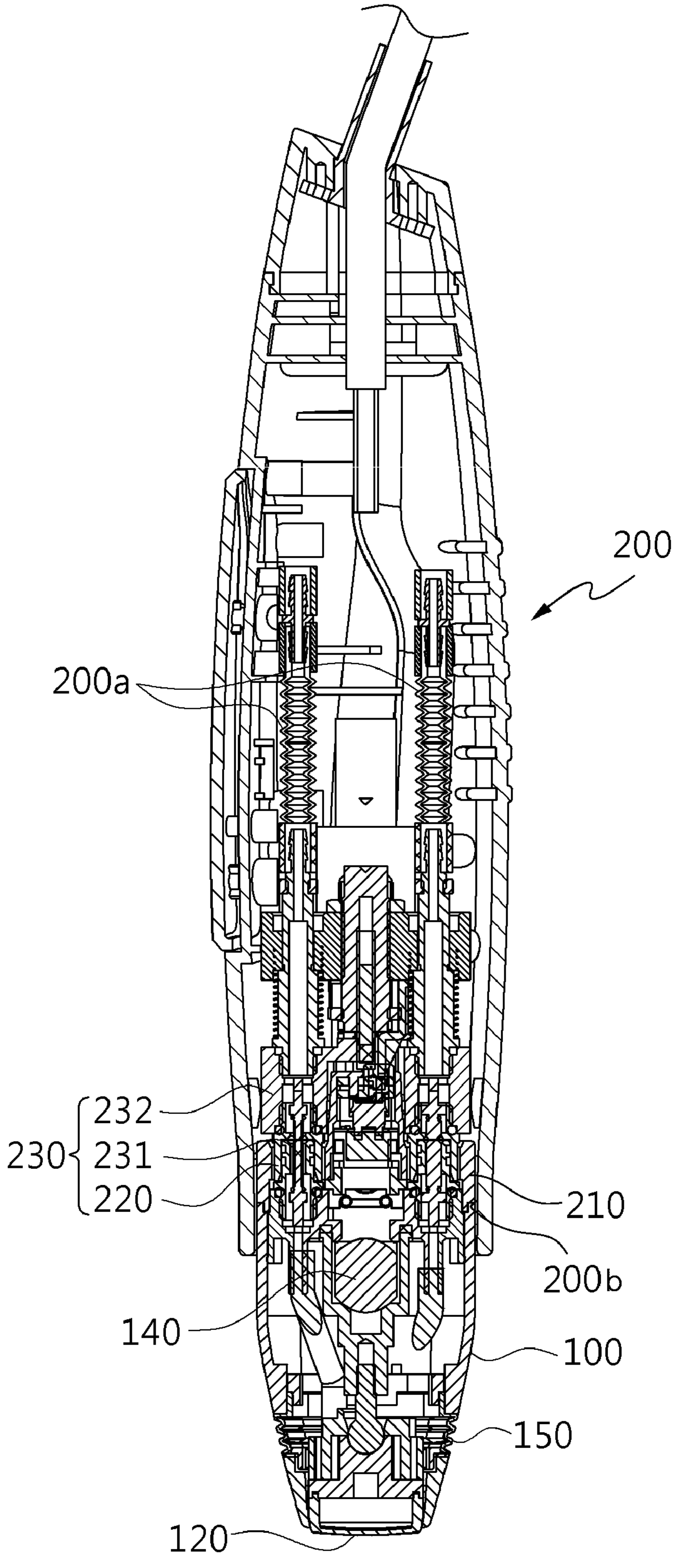
FIG. 5 is a sectional view showing the embodiment of a handpiece skin beauty care treatment provided with an RF electrode cartridge for skin beauty care treatment according to the present disclosure.
Figure 6:
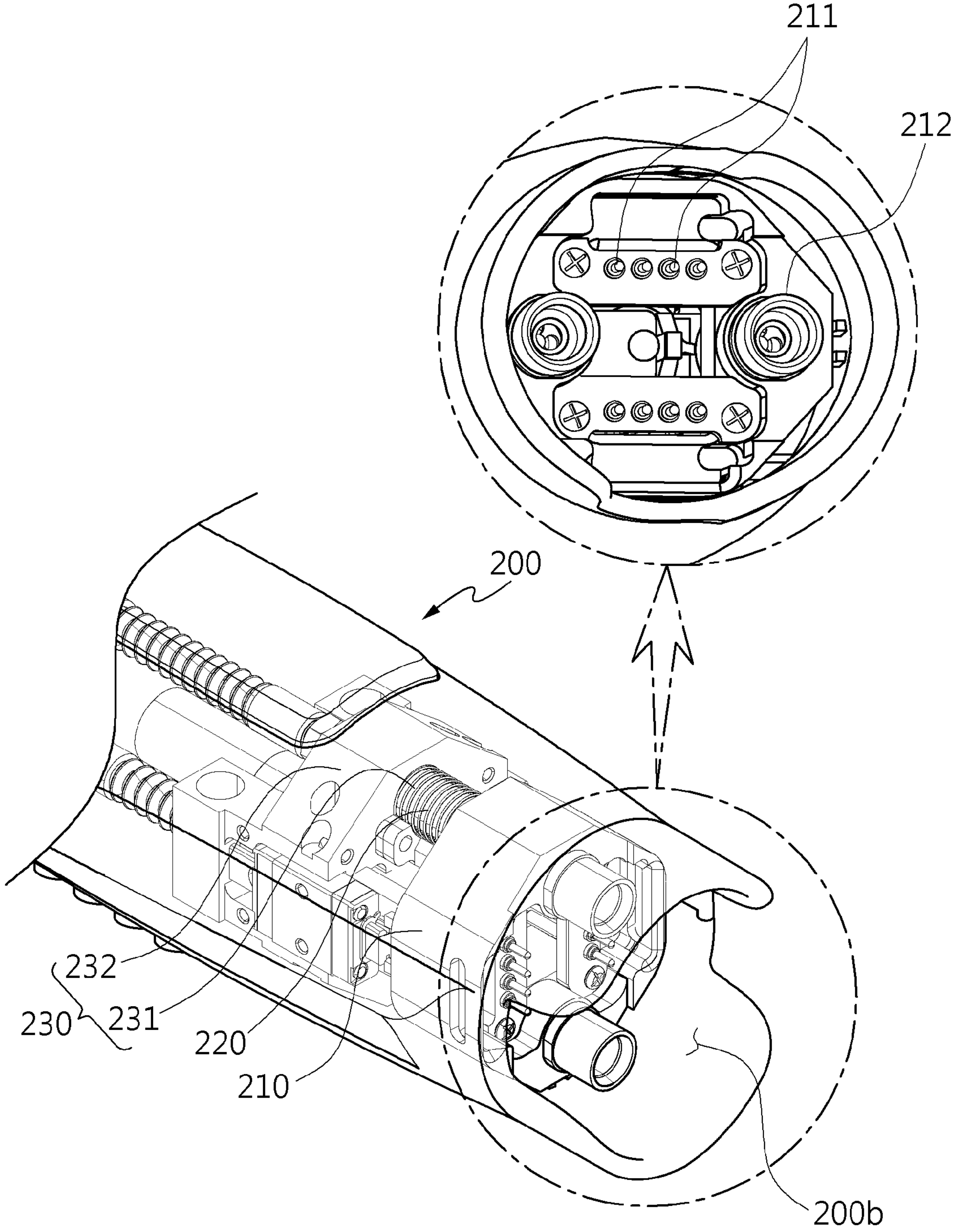
FIG. 6 is an enlarged perspective view of a main portion showing the embodiment of a handpiece skin beauty care treatment provided with an RF electrode cartridge for skin beauty care treatment according to the present disclosure.

FIG. 5 is a sectional view showing the embodiment of a handpiece skin beauty care treatment provided with an RF electrode cartridge for skin beauty care treatment according to the present disclosure, and FIG. 6 is an enlarged perspective view of a main portion showing the embodiment of a handpiece skin beauty care treatment provided with an RF electrode cartridge for skin beauty care treatment according to the present disclosure.

With reference to FIGS. 5 and 6, in the cartridge insertion part 200*b* positioned at the fore tip part of the handpiece main body casing 200, a second connection terminal part 211 to which the first connection terminal 121*a* is connected is positioned, and the cartridge coupling block 210 in which the line connection part 212 connecting the first coolant line part 170 and the second coolant line part 180 to the coolant circulation line parts 200*a*, respectively, is positioned is movably positioned.

The first connection terminal 121*a* is electrically connected to the control main body through the second connection terminal part 211 and a connection cable.

When the RF cartridge is inserted into the cartridge insertion part 200*b*, the first connection terminal 121*a* is connected to the second connection terminal part 211 of the cartridge coupling block 210, and the first coolant line part 170 and the second coolant line part 180 are connected to the coolant circulation line parts 200*a*, respectively, while being inserted into the line connection parts 212 of the cartridge coupling block 210 and fitted, respectively.

In addition, the cartridge coupling block 210 is positioned to be movable in the longitudinal direction of the handpiece main body casing 200, and a spring member 220 for a cartridge elastically supporting the cartridge coupling block 210 is positioned inside the handpiece main body casing 200.

The coolant circulation line part 200*a* may be a hose that may be freely bent with an extra length of at least as long as a moving distance of the RF electrode cartridge 100 within the handpiece main body casing 200 or a hose having a bellows structure that may be adjusted in length within the handpiece main body casing 200.

When the RF electrode body 120 is brought into close contact with the patient's skin to press, the spring member 220 for the cartridge elastically supports the movable cartridge coupling block 210 coupled with the RF electrode cartridge 100, thereby serving to buffer loads applied to the patient, and pushes the RF electrode cartridge 100 to the patient's skin side with an elastic restoring force so that the RF electrode body 120 may be more completely brought into close contact with the patient's skin.

A cartridge movement guide part 230 configured to guide a linear movement of the cartridge coupling block 210 is positioned inside the handpiece main body casing 200.

The cartridge movement guide part 230 may include a movement guide bar part 231 positioned to protrude from the cartridge coupling block 210 and a movement guide block 232 positioned inside the handpiece main body casing 200 and with which the guide bar part 231 is coupled to be movable by passing therethrough.

In addition, as an example, a plurality of the movement guide bar parts 231 is provided, and at least any one of the plurality of the movement guide bar parts is positioned passing through the spring member 220 for a cartridge, which is a coil spring.

That is, the spring member 220 for a cartridge is the coil spring as an example, and the movement guide bar part 231 is positioned by passing therethrough. In addition, the spring member 220 for a cartridge has one end part side supported by the cartridge insertion part 200*b* and an opposite end part side supported by the movement guide block 232, thereby elastically supporting the linear movement of the cartridge coupling block 210 and the RF electrode cartridge 100 coupled to the cartridge coupling block 210.

The RF electrode cartridge 100 for skin beauty care treatment and the handpiece for skin beauty care treatment provided with the same according to the present disclosure operate a procedure while moving the RF electrode body 120 in a state in which the RF electrode body 120 is brought in close contact with the patient's skin.

At this time, while being freely tilted for all ranges of 360 angle degrees around the ball joint part 140 within the radius thereof, the first casing part 110*a* of the RF electrode cartridge 100 enables the RF electrode body 120 to be continuously maintained by being brought into close contact with the skin.

In addition, the vibrations by the vibration motor unit 160 generate a massage effect on the skin to further induce a therapeutic effect according to the procedure.

In addition, the spring member 220 for the cartridge buffers the pressing force pressed by the operator by elastic support, and in along with, the state in which the RF electrode body 120 is brought into close contact with the skin may be kept more reliably by the elastic restoring force of the spring member 220 for the cartridge.

In the present disclosure, while being freely tilted for all ranges of 360 angle degrees around a ball joint part 140 within a radius thereof, the RF electrode body 120 moves in a state of being brought into close contact with the skin during the procedure, thereby preventing an accident that may occur while the RF electrode body 120 is spaced apart from the skin and in which damage to the skin tissue or burns to the skin may be caused. Accordingly, the present disclosure greatly improves safety during the procedure.

In the present disclosure, the operator may freely move the RF electrode body being brought into close contact with the skin with an appropriate force during the procedure, whereby the operator's convenience is secured, and the patient's discomfort due to excessive pressure is prevented to greatly improve patient's satisfaction with a procedure.

It should be noted that the present disclosure is not limited to the above-described embodiment and may be implemented with various modifications without departing from the gist of the present disclosure, wherein such modifications are included in the configuration of the present disclosure.

The invention claimed is:

1. An RF electrode cartridge for skin beauty care treatment, the cartridge comprising:
- a cartridge casing; and
- an RF electrode body positioned on one surface of the cartridge casing and being brought into contact with skin to apply RF energy inside the skin,
- wherein the cartridge casing includes:
  - a first casing part on one surface of which the RF electrode body is positioned;
  - a second casing part to which the first casing part is connected to be tiltable;
  - a ball joint part connecting the first casing part and the second casing part, thereby allowing the first casing part to be freely tilted for all ranges of 360 angle degrees within a radius of the first casing part; and
  - a bellows member having one end part side connected to the first casing part and an opposite end part side connected to the second casing part, positioned to surround the ball joint part, and provided with a plurality of corrugation parts,
- wherein the bellows member has one end part side fixed along an outer periphery of the first casing part and an opposite end part side fixed along an outer circumference of the second casing part, thereby surrounding an outer side of the ball joint part positioned in a center at a spaced apart position.

2. The cartridge of claim 1, wherein the RF electrode body comprises:
- an RF electrode member positioned on one surface of the first casing part and provided in a curved convex surface as a conductor to apply RF energy to the skin; and an insulation film member covering a surface of the RF electrode member.

3. The cartridge of claim 2, wherein the RF electrode member is a plating layer integrally provided in plating on one surface of the first casing part.

4. The cartridge of claim 1, wherein a cooling space filled with coolant for cooling the RF electrode body is positioned inside the first casing part, the RF electrode body is provided with a first connection terminal that protrudes upward and is electrically connected to an RF signal generator of a control main body, and a terminal passage through which the first connection terminal passes is provided in the cooling space, and a terminal insulation part is positioned to insulate the first connection terminal from the coolant in the cooling space.

5. The cartridge of claim 4, wherein, in the cooling space protruding integrally from a bottom surface of the cooling space and having an upper end part side thereof connected to a cooling space cover part that seals an upper part of the cooling space, thereby being sealed, the terminal insulation part has a structure insulating the coolant and the first connection terminal.

6. The cartridge of claim 1, further comprising:

a vibration motor unit positioned inside the cartridge casing.

7. The cartridge of claim 1, wherein a cooling space filled with coolant for cooling the RF electrode body is positioned inside the first casing part, a first coolant line part and a second coolant line part supplying the coolant into the cooling space and discharging the coolant inside the cooling space so as to circulate the coolant are further comprised, and a temperature sensor configured to sense temperature of the coolant is positioned inside the cooling space.

* * * * *